(12) United States Patent
Harlev et al.

(10) Patent No.: US 8,401,625 B2
(45) Date of Patent: Mar. 19, 2013

(54) MULTI-ELECTRODE MAPPING SYSTEM

(75) Inventors: Doron Harlev, Brookline, MA (US); Zsolt Badics, Andover, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 0 days.

(21) Appl. No.: 13/185,699

(22) Filed: Jul. 19, 2011

(65) Prior Publication Data

US 2011/0275949 A1 Nov. 10, 2011

Related U.S. Application Data

(62) Division of application No. 12/428,838, filed on Apr. 23, 2009.

(51) Int. Cl.
*A61B 5/02* (2006.01)
*A61B 5/04* (2006.01)
*A61N 1/39* (2006.01)
*A61N 1/00* (2006.01)

(52) U.S. Cl. ........ 600/509; 600/508; 600/510; 600/512; 607/9; 607/27; 607/28

(58) Field of Classification Search .......... 600/508–528; 607/9, 27, 28
See application file for complete search history.

(56) References Cited

U.S. PATENT DOCUMENTS

| | | | |
|---|---|---|---|
| 4,649,924 A | 3/1987 | Taccardi | 128/642 |
| 4,674,518 A | 6/1987 | Salo | 128/695 |
| 4,840,182 A | 6/1989 | Carlson | 128/694 |
| 4,920,490 A | 4/1990 | Isaacson | 364/413.13 |
| 5,156,151 A | 10/1992 | Imran | |
| 5,284,142 A | 2/1994 | Goble et al. | 128/653.1 |
| 5,297,549 A | 3/1994 | Beatty et al. | 128/642 |
| 5,300,068 A | 4/1994 | Rosar et al. | |
| 5,341,807 A | 8/1994 | Nardella | 128/642 |
| 5,381,333 A | 1/1995 | Isaacson et al. | 364/413.13 |
| 5,469,858 A | 11/1995 | Osborne | |
| 5,480,422 A | 1/1996 | Ben-haim | 607/122 |
| 5,500,011 A | 3/1996 | Desai | 607/116 |
| 5,553,611 A | 9/1996 | Budd et al. | 128/642 |
| 5,568,809 A | 10/1996 | Ben-Haim | 128/656 |
| 5,577,502 A | 11/1996 | Darrow et al. | 128/653.1 |
| 5,588,429 A | 12/1996 | Isaacson et al. | |
| 5,662,108 A | 9/1997 | Budd et al. | 128/642 |
| 5,687,737 A | 11/1997 | Branham et al. | 128/710 |
| 5,697,377 A | 12/1997 | Wittkampf | 128/696 |
| 5,704,365 A | 1/1998 | Albrecht et al. | |
| 5,722,402 A | 3/1998 | Swanson et al. | 128/642 |
| 5,840,025 A | 11/1998 | Ben-Haim | |
| 5,840,031 A | 11/1998 | Crowley | |

(Continued)

FOREIGN PATENT DOCUMENTS

WO 2010/123637 10/2010

OTHER PUBLICATIONS

Adams et al., "Seeded Region Growing", *IEEE Transactions on Pattern Analysis and Machine Intelligence*, 16(6):641-647, 1994.

(Continued)

*Primary Examiner* — Niketa Patel
*Assistant Examiner* — Lindsey G Hankins
(74) *Attorney, Agent, or Firm* — Fish & Richardson P.C.

(57) ABSTRACT

In some aspects, a method includes measuring unipolar signals at one or more electrodes in response to electrical activity in a heart cavity. The method also includes determining, based at least in part on Laplace's equation, bipolar physiological information at multiple locations of an surface based on the measured unipolar signals and positions of the one or more electrodes with respect to the surface.

32 Claims, 6 Drawing Sheets

U.S. PATENT DOCUMENTS

| | | | |
|---|---|---|---|
| 5,846,198 A | 12/1998 | Killmann | |
| 5,848,972 A | 12/1998 | Triedman et al. | |
| 5,921,982 A | 7/1999 | Lesh et al. | |
| 5,954,665 A | 9/1999 | Ben-Haim | |
| 5,971,933 A | 10/1999 | Gopakumaran et al. | 600/526 |
| 5,983,126 A | 11/1999 | Wittkampf | |
| 6,050,267 A | 4/2000 | Nardella et al. | 128/899 |
| 6,095,150 A | 8/2000 | Panescu et al. | 128/899 |
| 6,167,296 A | 12/2000 | Shahidi | |
| 6,226,542 B1 | 5/2001 | Reisfeld | |
| 6,236,886 B1 | 5/2001 | Cherepenin et al. | |
| 6,240,307 B1 | 5/2001 | Beatty et al. | 600/374 |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | |
| 6,318,375 B1 | 11/2001 | Plicchi et al. | 128/899 |
| 6,360,123 B1 | 3/2002 | Kimichi et al. | 600/547 |
| 6,368,285 B1 | 4/2002 | Osadchy et al. | 600/508 |
| 6,400,981 B1 | 6/2002 | Govari | 600/509 |
| 6,516,807 B1 | 2/2003 | Panescu et al. | |
| 6,547,082 B1 | 4/2003 | Babini | 211/41.17 |
| 6,556,695 B1 | 4/2003 | Packer et al. | 382/128 |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | 342/448 |
| 6,600,948 B2 | 7/2003 | Ben-Haim et al. | |
| 6,603,996 B1 | 8/2003 | Beatty et al. | 600/513 |
| 6,631,290 B1 | 10/2003 | Guck et al. | |
| 6,640,119 B1 | 10/2003 | Budd et al. | 600/374 |
| 6,650,927 B1 | 11/2003 | Keidar | 600/424 |
| 6,690,963 B2 | 2/2004 | Ben-haim et al. | 600/424 |
| 6,701,176 B1 | 3/2004 | Halperin et al. | 600/411 |
| 6,728,562 B1 | 4/2004 | Budd et al. | |
| 6,773,402 B2 | 8/2004 | Govari et al. | |
| 6,807,439 B2 | 10/2004 | Edwards et al. | 600/420 |
| 6,839,588 B1 | 1/2005 | Rudy | 600/523 |
| 6,847,839 B2 | 1/2005 | Ciaccio et al. | |
| 6,872,428 B2 | 3/2005 | Yang et al. | 427/568 |
| 6,892,090 B2 | 5/2005 | Verard et al. | |
| 6,892,091 B1 | 5/2005 | Ben-Haim et al. | |
| 6,939,309 B1 | 9/2005 | Beatty et al. | 600/508 |
| 6,978,168 B2 | 12/2005 | Beatty et al. | 600/513 |
| 6,990,370 B1 | 1/2006 | Beatty et al. | 600/509 |
| 7,016,719 B2 | 3/2006 | Rudy et al. | |
| 7,263,397 B2 | 8/2007 | Hauck et al. | 600/374 |
| 7,505,810 B2 | 3/2009 | Harley et al. | |
| 7,515,954 B2 | 4/2009 | Harley et al. | |
| 7,729,752 B2 | 6/2010 | Harley et al. | |
| 2002/0151807 A1 | 10/2002 | Goldin | |
| 2003/0018251 A1 | 1/2003 | Solomon | 600/427 |
| 2003/0065271 A1 | 4/2003 | Khoury | 600/509 |
| 2003/0076277 A1 | 4/2003 | Muramatsu et al. | 345/1.1 |
| 2003/0216630 A1 | 11/2003 | Jersey-Willuhn et al. | |
| 2004/0077942 A1 | 4/2004 | Hall et al. | 600/428 |
| 2004/0097806 A1 | 5/2004 | Hunter et al. | 600/434 |
| 2004/0243015 A1* | 12/2004 | Smith et al. | 600/511 |
| 2004/0254437 A1 | 12/2004 | Hauck et al. | 600/374 |
| 2005/0038337 A1 | 2/2005 | Edwards | 600/424 |
| 2005/0054918 A1 | 3/2005 | Sra | 600/427 |
| 2005/0107834 A1* | 5/2005 | Freeman et al. | 607/5 |
| 2005/0154282 A1 | 7/2005 | Li et al. | 600/407 |
| 2005/0288599 A1 | 12/2005 | MacAdam et al. | |
| 2006/0085049 A1 | 4/2006 | Cory et al. | 607/48 |
| 2006/0116575 A1 | 6/2006 | Willis | 600/434 |
| 2006/0122526 A1 | 6/2006 | Berenfeld et al. | |
| 2006/0173251 A1 | 8/2006 | Govari et al. | 600/306 |
| 2006/0178587 A1 | 8/2006 | Khoury | |
| 2006/0241401 A1 | 10/2006 | Govari et al. | 600/424 |
| 2007/0016007 A1 | 1/2007 | Govari et al. | 600/424 |
| 2007/0038078 A1 | 2/2007 | Osadchy | 600/424 |
| 2007/0049821 A1 | 3/2007 | Willis | |
| 2007/0197929 A1 | 8/2007 | Porath et al. | |
| 2007/0265539 A1* | 11/2007 | Hastings et al. | 600/513 |
| 2007/0287902 A1 | 12/2007 | Fuimaono et al. | |
| 2007/0299351 A1 | 12/2007 | Harlev et al. | 600/509 |
| 2008/0190438 A1 | 8/2008 | Harley et al. | |
| 2008/0221566 A1* | 9/2008 | Krishnan | 606/41 |
| 2008/0249424 A1 | 10/2008 | Harlev et al. | |
| 2009/0171274 A1 | 7/2009 | Harley et al. | |
| 2009/0177072 A1 | 7/2009 | Harley et al. | |

OTHER PUBLICATIONS

Search Report and Written Opinion in PCT/US2010/027568, mailed Nov. 4, 2010, 8 pages.

Baan, Jan et al., "Continuous Measurement Of Left Ventricular Volume In Animals And Humans By Conductance Catheter", Circulation, vol. 70,pp. 812-823.

Ben-Haim et al., "Nonfluoroscopic, in Vivo Navigation and Mapping Technology", Nature Medicine, 2(12):1393-1395, 1996.

Besl et al., "A Method for Registration of 3-D Shapes", IEEE Transactions on Pattern Analysis and Machine Intelligence, 14(2):239-256, 1992.

Blomström-Lundqvist et al., "ACC/AHA/ESC Guidelines for the Management of Patients With Supraventricular Arrhythmias—Executive Summary", Journal of the American College of Cardiology, 42(8):1493-1531, 2003.

Breithardt et al., "AHA Medical/Scientific Statement—Special Report: Standards for Analysis of Ventricular Late Potentials Using High-Resolution or Signal-Averaged Electrocardiography", Circulation, 83(4):1481-1488, 1991.

Brooks et al., "Electrical Imaging of the Heart", IEEE Signal Processing Magazine, pp. 24-42, 1997.

Caspi et al., "Stem Cell Research: Regenerating the Heart Using Human Embryonic Stem Cells—from Cell to Bedside", IMAJ, 8:208-214, 2006.

De Groot et al., "Three-Dimensional Catheter Positioning During Radiofrequency Ablation in Patients: First Application of a Real-Time Position Management System", Journal of Cardiovascular Electrophysiology, 11:1183-1192, 2000.

Donahue et al., "Focal Modification of Electrical Conduction in the Heart by Viral Gene Transfer", Nature Medicine, 6(12):1395-1398, 2000.

Dong et al., "Integrated Electroanatomic Mapping With Three-Dimensional Computed Tomographic Images for Real-Time Guided Ablations", Circulation, 113:186-194, 2006.

Durrer et al., "Total Excitation of the Isolated Human Heart", Circulation, vol. XLI, pp. 899-912, 1970.

Ector, Joris et al., "Cardiac Three-Dimensional Magnetic Resonance Imaging And Fluoroscopy Merging", Circulation, (Dec. 13, 2005).

Friedman, "Catheter Cryoablation of Cardiac Arrhythmias", Current Opinion in Cardiology, 20:48-54, 2005.

Friedman, "Novel Mapping Techniques for Cardiac Electrophysiology", Heart, 87:575-582, 2002.

Geddes, L.A. et al., "Criteria for the Selection of Materials for Implanted Electrodes", Annals of Biomedical Engineering, vol. 31, pp. 879-890 (2003).

Gepstein et al., "A Novel Method for Nonfluoroscopic Catheter-Based Electroanatomical Mapping of the Heart", Circulation 95:1611-1622, 1997.

Huang, Yi-Chih et al., "Development Of A Third Generation Intraventricular Impedance Imaging (Iii) System Evaluation Of Hardware Design", Engineering in Medicine and Biology Society,. Proceedings of the 19th Annual International Conference of the IEEE, Oct. 30-Nov. 2, 1997 vol. 6, (1997).

International Search Report and the Written Opinion, PCT/US07/70854, Sep. 12, 2008, 15 pages.

International Search Report and the Written Opinion, PCT/US08/52385, Aug. 8, 2008, 11 pages.

Jain et al., "Cell Therapy Attenuates Deleterious Ventricular Remodeling and Improves Cardiac Performance After Myocardial Infarction", Circulation, 103:1920-1927, 2001.

Jalife, "Rotors and Spiral Waves in Atrial Fibrillation", Journal of Cardiovascular Electrophysiology, 14:776-780, 2003.

Jané et al., "Alignment Methods for Averaging of High-Resolution Cardiac Signals: A Comparative Study of Performance", IEEE Transactions on Biomedical Engineering, 38(6):571-579, 1991.

Jia et al., "Electrophysiologic Endocardial Mapping From a Noncontact Nonexpandable Catheter: A Validation Study of a Geometry-Based Concept", *Journal of Cardiovascular Electrophysiology*, 11:1238-1251, 2000.

Kikuchi et al., "Targeted Modification of Atrial Electrophysiology by Homogeneous Transmural Atrial Gene Transfer", *Circulation*, 111:264-270, 2005.

Kistler et al., "Validation of Three-Dimensional Cardiac Image Integration: Use of Integrated CT Image into Electroanatomic Mapping System to Performa Catheter Ablation of Atrial Fibrillation", *Journal of Cardiovascular Electrophysiology*, 17:341-348, 2006.

Kun, Stevan et al., "Conductance Volumetric Model of an Eccentrically Positioned Catheter Within a Three-Compartment Ellipsoidal Ventricle", U, IEEE Transactions on, Jun. 1993, vol. 40, Issue: 6.

Laciar et al., "Improved Alignment Method for Noisy High-Resolution ECG and Holter Records Using Multiscale Cross-Correlation", *IEEE Transactions on Biomedical Engineering*, 50(3):344-353, 2003.

Liu et al., "Endocardial Potential Mapping From a Noncontact Nonexpandable Catheter: A Feasibility Study", *Annals of Biomedical Engineering*, 26:994-1009, 1998.

Lorensen et al. "Marching Cubes: A High Resolution 3D Surface Construction Algorithm". *Computer Graphics* 21(4):163-169, Jul. 1987.

Mäkelä et al., "A Review of Cardiac Image Registration Methods", *IEEE Transactions on Medical Imaging*, 21(9):1011-1021, 2002.

Malladi, R. et al., "A Geometric Approach To Segmentation And Analysis Of 3D Medical Images", Mathematical Methods in Biomedical Image Analysis, Proceedings of the Workshop on, Jun. 21-22, 1996, pp. 244-252, (1996).

Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).

Meininger et al., "Initial Experience with a Novel Focused Ultrasound Ablation System for Ring Ablation Outside the Pulmonary Vein", *Journal of Interventional Cardiac Electrophysiology*, 8:141-148, 2003.

Merrill, Daniel R. et al., "Electrical stimulation of excitable tissue: design of efficacious and safe protocols", Journal of Neuroscience Methods, vol. 141, pp. 171-198 (2005).

Miller, "Editor's Forum—Application of Registration for Ablation: A Marriage of Technologies", *Journal of Interventional Cardiac Electrophysiology*, 11:87-89, 2004.

Nademanee et al., "A New Approach for Catheter Ablation of Atrial Fibrillation: Mapping of the Electrophysiologic Substrate", *Journal of the American College of Cardiology*, 43(11):2044-2053, 2004.

Noseworthy et al., "The Impact of Respiration on Left Atrial and Pulmonary Venous Anatomy: Implications for Image-Guided Intervention", *Heart Rhythm*, 2:1173-1178, 2005.

Notification of Transmittal of the International Search Report and the Written Opinion of the International Searching Authority, or the Declaration, PCT/US2009/036099, Dated Apr. 28, 2009, 21 pages.

Pappone et al., "Robotic Magnetic Navigation for Atrial Fibrillation Ablation", *Journal of the American College of Cardiology*, 47(7):1390-1400, 2006.

Paragios, "A Level Set Approach for Shape-Driven Segmentation and Tracking of the Left Ventricle", *IEEE Transactions on Medical Imaging*, 22(6):773-776, 2003.

Persson et al., "A Simple Mesh Generator in MATLAB", *SIAM Review*, 46(2):329-345, 2004.

Persson, "Mesh Generation for Implicit Geometries", *Massachusetts Institute of Technology—Thesis*, Feb. 5, 2006.

Pham, Dzung et al., "Current Methods in Medical Image Segmentation", Annu. Rev. Biomed. Eng., 02: pp. 315-337, (2000).

Rao et al., "Novel Noncontact Catheter System for Endocardial Electrical and Anatomical Imaging", *Annals of Biomedical Engineering*, 32(4):573-584, 2004.

Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", *Journal of the American College of Cardiology*, 44(11):2202-2213, 2004.

Reddy et al., "Use of a Diode Laser Balloon Ablation Catheter to Generate Circumferential Pulmonary Venous Lesions in an Open-Thoracotomy Caprine Model", *PACE*, 27:52-57, 2004.

Sanders et al., "Spectral Analysis Identifies Sites of High-Frequency Activity Maintaining Atrial Fibrillation in Humans", *Circulation*, 112:789-797, 2005.

Sethian. "Level Set Methods and Fast Marching Methods: Evolving Interfaces in Computational Geometry, Fluid Mechanics, Computer Vision, and Materials Science". *Department of Mathematics—University of California, Berkeley*. Cambridge University Press, 1999.

Simon et al., "Electroanatomic Mapping of the Right Atrium With a Right Atrial Basket Catheter and Three-Dimensional Intracardiac Echocardiography", *PACE*, 27:318-326, 2004.

Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.

Solomon et al., "Real-Time Cardiac Catheter Navigation on Three-Dimensional CT Images", *Journal of Interventional Cardiac Electrophysiology*, 8:27-36, 2003.

Sra et al., "Registration of Three-Dimensional Left Atrial Computed Tomographic Images With Projection Images Obtained Using Fluoroscopy", *Circulation*, 112:3763-3768, 2005.

Sra, Jasbir et al, "Registration Of 3D Computed Tomographic Images With Interventional Systems: Implications For Catheter Ablation Of Atrial Fibrillation", J Interv Card Electrophysiol, 16: pp. 141-148, (2006).

Stevenson, "Radiofrequency Catheter Ablation of Ventricular Tachycardia After Myocardial Infarction", *Circulation*, 98:308-314, 1998.

Taccardi et al., "A New Intracavitary Probe for Detecting the Site of the Origin of Ectopic Ventricular Beats During One Cardiac Cycle", *Circulation*, 75(1):272-281, 1987.

Thal et al., "Novel Applications in Catheter Ablation", *Journal of Interventional Cardiac Electrophysiology*, 13:17-21, 2005.

Thiagalingam et al., "Noncontact Mapping of the Left Ventricle: Insights from Validation With Transmural Contact Mapping", *PACE*, 27:570-578, 2004.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf et al., "LocaLisa: New Technique for Real-Time 3-Dimensional Localization of Regular Intracardiac Electrodes", *Circulation*, 99:1312-1317, 1999.

Yezzi, Anthony et al., "A Geometric Snake Model for Segmentation", IEEE Transactions on Medical Imaging, vol. 16, No. 2, (Apr. 1997).

Arthur, "Clinical Use of Intracardiac Impedance: Current Applications and Future Perspectives", PACE, vol. 24:500-506, Apr. 2001.

International Search Report and Written Opinion in PCT/US2010/027568, mailed Nov. 4, 2010, 8 pages.

Badics, "Real-Time Reconstruction of Endocardial Potential Maps in Non-Contact Cardiac Mapping", International Journal for computation and Mathematics in Electrical Engineering (COMPEL), vol. 28, No. 4, 2009.

Cheney et al., "Electrical Impedance Tomography", SIAM Review 41:85-101, 1999.

E.J. Haug, K. K. Choi, V. Komkov: Design Sensitivity Analysis of Structural Systems, Mathematics in Science and Engineering, vol. 177 (1986).

Kuklik et al., "The reconstruction, from a set of points, and analysis of the interior surface of the heart chamber", Physiol. Meas. 25:617-627, 2004.

L. Piegl, W. Tiller: The NURBS Book, 2nd Edition, Springer (1997).

International Preliminary Report on Patentability in PCT/US2010/027568, mailed Nov. 3, 2011, 5 pages.

\* cited by examiner

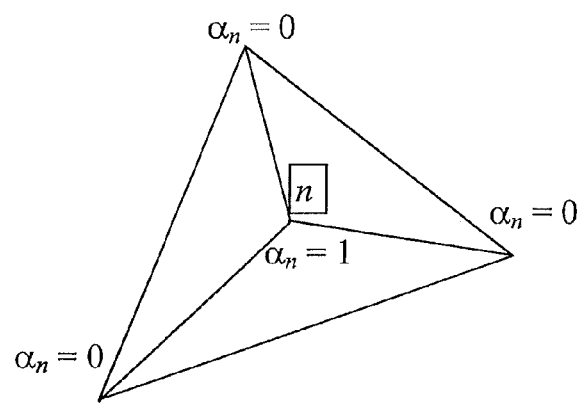
FIG. 7
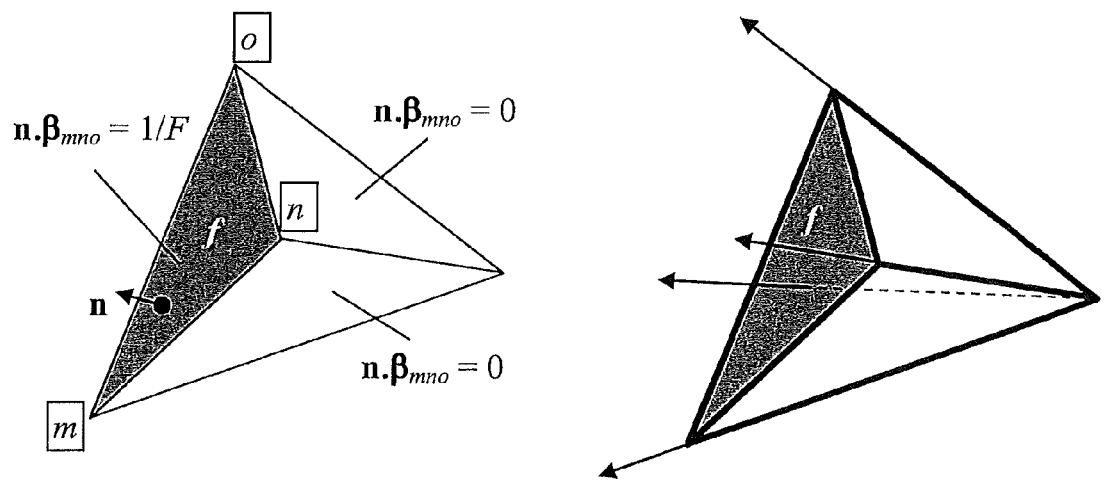
FIG. 8A
FIG. 8B

MULTI-ELECTRODE MAPPING SYSTEM

CROSS-REFERENCE TO RELATED APPLICATIONS

This application is a divisional (and claims the benefit of priority under 35 U.S.C. §121) of U.S. Application Ser. No. 12/428,838, filed Apr. 23, 2009 and entitled "MULTI-ELECTRODE MAPPING SYSTEM." The disclosure of the prior application is considered part of (and is incorporated by reference in its entirety) the disclosure of this application.

TECHNICAL FIELD

This invention relates to the determination and representation of physiological information relating to a heart surface using, e.g., a non-contact catheter.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional 3D mapping techniques include contact mapping and non-contact mapping. In contact mapping techniques one or more catheters are advanced into the heart. Physiological signals resulting from the electrical activity of the heart are acquired with one or more electrodes located at the catheter distal tip after determining that the tip is in stable and steady contact with the endocardium surface of a particular heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm. On the other hand, in non-contact-based mapping systems a multiple electrodes catheter is percutaneously placed in the heart chamber of interest. Once in the chamber, the catheter is deployed to assume a 3D shape. Using the signals detected by the non-contact electrodes and information on chamber anatomy and relative electrode location, the system provides physiological information regarding the endocardium of the heart chamber.

SUMMARY

In some aspects a method includes measuring physiological signals at one or more electrodes in response to electrical activity in a heart cavity. The hear cavity having a surface. The method also includes determining, based at least in part on Laplace's equation, bipolar physiological information at multiple locations of a surface based on the measured physiological signals and positions of the one or more electrodes with respect to the surface.

Embodiments can include one or more of the following.

The physiological signals can be unipolar signals such as unipolar potential signals.

Measuring the physiological signals can include measuring a potential between a first electrode and a second electrode. The first electrode can be located within the heart cavity and the second electrode can be located at a distance from the heart cavity such that the electrode is not affected by local tissue activation in a heart cavity.

Measuring the physiological signals can include measuring a potential between the first electrode and the second electrode that are separated by a distance greater than 5 cm. Measuring the physiological signals can include measuring a potential between the first electrode and the second electrode that are separated by a distance greater than 10 cm. Measuring the physiological signals can include measuring a potential between the first electrode and the second electrode that are separated by a distance greater than 15 cm.

The bipolar physiological information can be current density information. The current density information can include a normal component of the current density. The current density information can include a magnitude of a current density vector. The current density information can include a magnitude of a tangential component of the current density.

Measuring the physiological signals can include measuring the physiological signals for multiple different catheter positions in the heart cavity. The number of catheter positions at which the signals are measured and used to determine the bipolar physiological information at the multiple locations of the endocardium surface can be more than three.

The signals can be measured for at least one electrical heart cycle for each catheter position.

The determination of the physiological information at the multiple locations of the endocardium surface can include synchronizing the signals measured at the different catheter positions with one another according to an electrical heart beat cycle. The measured signals can be synchronized based on physiological data including at least one of: ECG and intercardiac electrograms.

The determination of the physiological information at the multiple locations of the endocardium surface can include processing the synchronized signals as though they were obtained at one time from all of the positions sampled by the catheter electrodes for the different positions of the catheter in the heart cavity.

Determining the bipolar physiological information can include applying a transformation function to the measured physiological signals. Applying the transformation function can include solving directly for current. Solving directly for current can include using finite element analysis. Applying the transformation function can include solving simultaneously for current and potential. Solving simultaneously for current and potential can include using finite element analysis. Solving simultaneously for current and potential can include solving a transformation function which can be expressed as one or more matrices. One or more matrices can be represented by the following equation:

$$\begin{bmatrix} K_{TT} & K_{T,\tilde{c}e} \\ K_{aT} & 0 \end{bmatrix} \begin{bmatrix} J_T \\ \Phi_{\tilde{c}e} \end{bmatrix} = \begin{bmatrix} K_{Tc} & 0 \\ 0 & 0 \end{bmatrix} \begin{bmatrix} V_c \\ 0 \end{bmatrix}.$$

The one or more matrices can be further represented by one or more regularization terms.

Determining the bipolar physiological information at multiple locations of the endocardium surface can include applying a transformation function to the physiological signals, wherein the transformation functions relates the physiological signals to the physiological information at the multiple locations of the endocardium surface. Determining the bipolar physiological information can include determining the transformation function by calculating a forward transformation for relating the physiological information at the multiple locations to the signals measured and inverting the forward transformation. Inverting the forward transformation can include reformulating an underdetermined matrix inversion by regularization. The regularization can be based on a physical relationship. The physical relationship can be a relationship between current and potential. The physical relationship can be represented by the following equation: $[K_{a,\tilde{c}e}][\Phi_{\tilde{c}e}]=-[K_{ac}][V_c]$. The regularization further can also include limiting the current density magnitude. The regularization can be a volumetric regularization.

The one or more electrodes can include multiple spatially distributed electrodes mounted on one or more catheters that are placed inside the heart cavity.

During the measurement of the physiological signals, at least some of the electrodes can be spaced apart from the endocardium surface and/or during the measurement of the physiological signals, at least some of the electrodes can be in contact with the endocardium surface.

The one or more electrodes can include one or more body-surface electrodes. The one or more electrodes can include both electrodes mounted on one or more catheters that are placed inside the body and body-surface electrodes. The one or more electrodes can include electrodes mounted on the one or more catheters that can be moved and positioned at multiple locations in an organ.

The method can also include displaying at least a portion of the determined physiological information. The physiological information can include electrical information.

The method can also include using the determined physiological information to guide treatment of the heart cavity. The treatment can include ablation of one or more selected regions of the heart. The method can also include repeating the measurement of catheter electrode signals and the determination of the physiological information after the ablation treatment. The treatment can include cell therapy, gene therapy, or the application of other biological agents.

The method can also include determining the positions of the electrodes with respect to the endocardium surface. Determining the positions of the electrodes with respect to the endocardium surface can include using at least one of electric fields, magnetic fields, fluoroscopy, and ultrasound to determine a position of the electrodes in a first coordinate system. Determining the positions of the electrodes with respect to the endocardium surface can include registering a representation of the endocardium surface with the first coordinate system. Determining the position of the electrodes can include measuring information about at least one of a position and orientation of the electrodes within the heart cavity. Determining the position of the electrodes can include using a tracking system to track the position of the electrodes. The tracking system can be a system that uses a magnetic field for tracking. The tracking system can be a system that uses injected currents for tracking.

The one or more electrodes can include multiple spatially distributed electrodes.

In some additional aspects, a system includes one or more electrodes configured to measure unipolar signals in response to electrical activity in a heart cavity having a surface and a processing unit configured to determine bipolar physiological information at multiple locations of the surface based on unipolar signals measured by the one or more electrodes and positions of the electrodes with respect to the surface.

Embodiments can include one or more of the following.

The unipolar signals can be unipolar potential signals.

The one or more electrodes can include at least a first electrode and a second electrode. The first electrode can be located within the heart cavity and the second electrode can be located at a distance from the heart cavity such that the electrode is not affected by local tissue activation in a heart cavity. The first and second electrodes can be configured to measure a potential between the first electrode and the second electrode.

The bipolar physiological information can include current density information. The current density information can include a normal component of the current density. The current density information can include a magnitude of a current density vector. The current density information can include a magnitude of a tangential component of the current density.

The processing unit can be further configured to synchronize signals measured at the different catheter positions with one another according to an electrical heart beat cycle. The processing unit can be further configured to synchronize the measured signals based on physiological data including at least one of: ECG and intercardiac electrograms.

The processing unit can be further configured to process the synchronized signals as though they were obtained at one time from all of the positions sampled by the catheter electrodes for the different positions of the catheter in the heart cavity.

The processing unit is further configured to apply a transformation function to the measured unipolar signals. The processing unit can be further configured to solve directly for current. The processing unit can be further configured to solve simultaneously for current and potential. The processing unit can be further configured to solve a transformation function which can be expressed as one or more matrices. The one or more matrices can include one or more regularization terms. The processing unit can be further configured to apply a transformation function to the unipolar signals. The transformation functions can relate the unipolar signals to the bipolar physiological information at the multiple locations of the endocardium surface.

The processing unit can be further configured to determine the transformation function by calculating a forward transformation for relating the physiological information at the multiple locations to the signals measured and inverting the forward transformation. The processing unit can be further configured to reformulate an underdetermined matrix inversion by regularization based on a physical relationship. The processing unit can be further configured to reformulate an underdetermined matrix inversion by a volumetric regularization.

The system can also include a display system configured to display at least a portion of the determined physiological information.

The electrodes can be mounted on one or more catheters that are placed inside the body. The electrodes can include one or more body-surface electrodes. The electrodes can include both electrodes mounted on one or more catheters that are placed inside the body and body-surface electrodes.

The system can also include a tracking system configured to obtain the positions of one or more electrodes. The tracking system can include a system using a magnetic field for tracking. The tracking system can include a system using injected currents for tracking.

The one or more electrodes can be multiple spatially distributed electrodes.

In some additional aspects, a method includes measuring electrical potentials at one or more electrodes in response to electrical activity in a heart cavity having a surface and determining current information at multiple locations of the surface based on the measured electrical potentials and positions of the one or more electrodes with respect to the surface.

Embodiments can include one or more of the following.

The current information can include a normal component of the current density. The current information can include a magnitude of a current density vector. The current information can include a magnitude of a tangential component of the current density.

Measuring the electrical potentials can include measuring the electrical potentials for multiple different catheter positions in a heart cavity having an endocardium surface. The electrical potentials can be measured for at least one electrical heart cycle for each of multiple catheter positions.

The determination of the current information at the multiple locations of the endocardium surface can include synchronizing the signals measured at the different catheter positions with one another according to an electrical heart beat cycle. The determination of the current information at the multiple locations of the endocardium surface further can include processing the synchronized signals as though they were obtained at one time from all of the positions sampled by the catheter electrodes for the different positions of the catheter in the heart cavity. Determining the current information can include applying a transformation function to the measured potential signals. Applying the transformation function can include solving directly for current. Solving directly for current can include using finite element analysis. Applying the transformation function can include solving simultaneously for current and potential. Solving simultaneously for current and potential can include using finite element analysis. Solving simultaneously for current and potential can include solving a transformation function which can be expressed as one or more matrices. The one or more matrices can be represented by the following equation:

$$\begin{bmatrix} K_{TT} & K_{T,\tilde{c}e} \\ K_{aT} & 0 \end{bmatrix} \begin{bmatrix} J_T \\ \Phi_{\tilde{c}e} \end{bmatrix} = \begin{bmatrix} K_{Tc} & 0 \\ 0 & 0 \end{bmatrix} \begin{bmatrix} V_c \\ 0 \end{bmatrix}.$$

The one or more matrices can be further represented by one or more regularization terms. Determining the current information at multiple locations of the endocardium surface can include applying a transformation function to the potential signals. The transformation function can relate the potential signals to the current information at the multiple locations of the endocardium surface. Determining the current information further can include determining the transformation function by calculating a forward transformation for relating the current information at the multiple locations to the potential signals measured and inverting the forward transformation. Inverting the forward transformation can include reformulating an underdetermined matrix inversion by regularization. The regularization can be based on a physical relationship. The physical relationship can be relationship between current and potential. The physical relationship can be represented by the following equation: $[K_{a,\tilde{c}e}][\Phi_{\tilde{c}e}] = -[K_{ac}][V_c]$. The regularization can also include limiting the current magnitude. The regularization can be a volumetric regularization.

In some additional aspects, a system includes one or more electrodes configured to measure electrical potentials in response to electrical activity in a heart cavity and a processing unit configured to determine current information at multiple locations of a surface based on unipolar signals measured by the one or more electrodes and positions of the electrodes with respect to the surface.

In some additional aspects, a method can include generating bipolar information based on three or more unipolar measurements.

Embodiments can include one or more of the following.

The unipolar measurements can be unipolar potential signals. The bipolar information can include current information. The bipolar information can current density information. The current density information can include a normal component of the current density. The current density information can include a magnitude of a current density vector. The current density information can include a magnitude of a tangential component of the current density.

The method can also include measuring the unipolar signals by measuring a potential between a first electrode and a second electrode, the first electrode being located within the heart cavity and the second electrode being located at a distance from the heart cavity such that the electrode is not affected by local tissue activation in a heart cavity.

The method can also include measuring the unipolar signals at one or more electrodes for multiple different catheter positions in the heart cavity in response to electrical activity in a heart cavity.

Generating bipolar information based on three or more unipolar measurements can include determining bipolar information at multiple locations of an endocardium surface based on the unipolar signals and positions of one or more electrodes used to measure the unipolar signals with respect to the endocardium surface.

Generating bipolar information can include applying a transformation function to the unipolar signals. Applying the transformation function can include solving directly for current. Applying the transformation function can include solving simultaneously for current and potential.

In some additional aspects, a system includes a processing unit configured to receive unipolar measurements and generate bipolar information based on three or more of the unipolar measurements.

Embodiments of the system may also include devices, software, components, and/or systems to perform any features described above in connection with the first method and/or described below in connection with the second method.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the descrip-

DESCRIPTION OF THE DRAWINGS

FIG. 7 is a schematic diagram of a first order node-based interpolation function.

FIG. 8A is schematic diagram of a facet-based vector interpolation function.

FIG. 8B is a schematic diagram of a vector field of the vector interpolation function of FIG. 8A.

Like reference symbols in the various drawings indicate like elements.

DETAILED DESCRIPTION

Embodiments disclosed herein include a method for generating non-contact electro-anatomical maps ("EAM") with bipolar or current density information. Prior methods for generating non-contact EAMs rely on generating EAMs with unipolar information.

Embodiments disclosed herein further describe a method for generating contact EAM with bipolar or current density information in locations that were not probed with a contact electrode.

In both methods (e.g., the non-contact method and the contact method), further post-processing operations can be performed on the reconstructed physiological information (e.g., the bipolar or current density information) to extract and display useful features of the bipolar or current density information.

In some embodiments, as described in more detail below, Laplace's Equation can be used for deriving the physiological information, sometimes using approximations or discretization methods. In addition, a volumetric regularization scheme that regularizes electrode measurements in addition to surface potentials can be used (e.g., as opposed to the use of surface regularization alone).

While the examples described herein focus on intracardiac endocardial mapping, the advantages of generating a bipolar non-contact map also hold for non-invasive body surface mapping which generate a bipolar epicardial EAM.

In general, when generating an EAM the physician is interested in relating electrical properties of tissue to anatomy. Two types of electrical measurements are typically performed to investigate electrical properties of tissue. The first is unipolar or potential measurement, $V_u$. In this case a voltage is measured between an investigated electrode and an "indifferent" electrode assumed to be far enough away so that it is not affected by local tissue activation (e.g., at least about 5 cm away from the investigated electrode, at least about 10 cm away from the investigated electrode, at least about 15 cm away from the investigated electrode, at least about 20 cm away from the investigated electrode, at least about 25 cm away from the investigated electrode, etc.). The "indifferent" electrode can be positioned inside the body, or derived from a surface potential such as Wilson's Central Terminal. The second type of measurement is bipolar measurement, $V_b$. In this case a voltage is measured between two close electrodes, usually a few millimeters (e.g., less than 3-5 mm) apart. In the bipolar case, both electrodes are in the heart and affected by local tissue activation. The bipolar measurement can be viewed as an estimation of the current density in the direction of the bipolar electrode pair.

Figure 1:
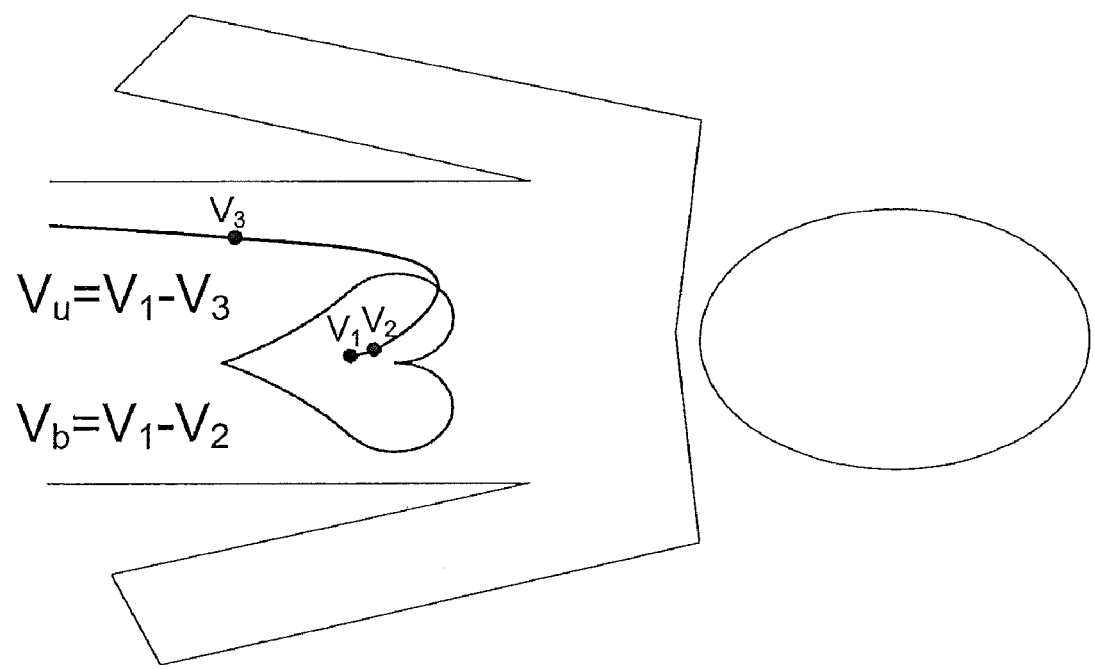
FIG. 1 is an exemplary schematic diagram of an arrangement for positioning electrodes in a patient's heart cavity.

Referring to FIG. 1, graphically represents the difference between unipolar and bipolar measurements. As noted above, in a unipolar measurement a potential measurement, $V_u$, is preformed between an investigated electrode (e.g., electrode V1) located inside the heart cavity and an "indifferent" electrode (e.g., electrode V3) located outside of the heart cavity and far enough away so that it is not affected by local tissue activation. As such, the potential measurement, $V_u$, for the unipolar measurement can be represented at $V_u$=V1–V3. As noted above, in a bipolar measurement a potential measurement, $V_b$, is measured between two close electrodes (e.g., electrodes V2 and V1) both of which are located within the heart cavity. As such, the potential measurement, Vb, for the bipolar measurement can be represented at $V_b$=V1–V2.

Both unipolar and bipolar measurements can be used in catheter ablation procedures. Bipolar measurements are believed to have a number of advantages over unipolar measurements. See, for example, Fred M. Kusumoto, "Unipolar Recording in Cardiac Electrophysiologic studies", *Journal of Interventional Cardiac Electrophysiology* 1999; 3.

One advantage of bipolar measurements is far field rejection. A goal of electro-anatomical mapping is to characterize the properties of underlying tissue in the vicinity of the measuring electrode. The far field is a field generated by tissue that is further from the point of interest, but is still large enough to affect measurement. Electrodes measure potential which results from a summation of all fields generated by tissue. In the unipolar case, it is estimated that the amplitude of measured signal is proportional to the reciprocal value of the square of the distance between tissue and the electrode. In the bipolar case it is estimated that the effect of distance is cubed. Therefore, bipolar measurements are better at measuring local tissue excitation and rejecting far field. Far field rejection can be of particular importance when mapping in the atria and when mapping in infracted tissue.

Another advantage of bipolar measurements is rejection of interference and noise. In the bipolar case, because the electrodes are spaced closely and their signal carrying wires are run down the catheter in close proximity, the effect of noise on the two electrodes has a large common component. Since electrode values are subtracted, much of the noise common to both electrodes can be rejected. Due to the larger distance between electrodes in the unipolar case, a smaller portion of the noise collected by electrodes is common, and less of it may be rejected. This leads to better signal to noise performance in the bipolar case.

Another advantage of bipolar measurements is the experience level and to accumulated knowledge about such measurements. Due to some of the advantages of bipolar measurements much experience and knowledge has been accumulated with bipolar measurements. For example, algorithms and methodologies that depend on specific bipolar threshold and signal behavior have been developed. To benefit from this body of knowledge and user experience it is important to provide bipolar EAM in a non-contact mapping system.

Methods for generating estimated unipolar measurements using non-contact mapping are described, for example, in U.S. Pat. No. 7,515,954 entitled "Non-contact cardiac mapping, including moving catheter and multi-beat integration" and filed Jun. 13, 2006 which is hereby incorporated in its entirety by reference. In contrast to generating estimated unipolar measurements, embodiments disclosed herein include systems and methods of directly and indirectly computing an estimation of bipolar measurement based on measured unipolar potential values (e.g., an estimation of a current density value). It is believed that one advantage of computing an estimation of bipolar measurement based on measured unipolar potential values is making available the advantages of bipolar mapping in a non-contact methodology. In addition, due to the nature of non-contact mapping and algorithms presented herein, it is also possible to provide current density maps, which can be viewed as mathematically ideal bipolar maps.

Embodiments disclosed herein include methods of performing regularization. In prior systems for generating EAM maps, due to the underdetermined ill-posed nature of the inverse problem surface regularization is applied such that a-priori assumptions regarding the distribution of the potential on the heart surface are used to constrain the estimated surface potential, for example, as described in U.S. Pat. No. 7,515,954 entitled "Non-contact cardiac mapping, including moving catheter and multi-beat integration" and filed Jun. 13, 2006 which is hereby incorporated in its entirety by reference. These a-priori assumptions are not governed by physical or biological laws, and therefore, add error to the solution in cases where actual surface distribution varies from the a-priori assumptions. Examples of such surface regularization schemes that employ these a-priory assumptions include Tikhonov 0 and 1 which limits signal or gradient magnitude. Embodiments disclosed herein include a regularization method which takes advantage of the physical relationship between current and potential and regularizes the relationship between those two estimated values. Since this method relies on the physical relationship between current and potential it is believed to greatly improve EAM accuracy.

It should be appreciated that the term non-contact as used herein is considered for any measurement that is not required to be on the surface of the cardiac chamber (e.g., measurements where the catheter is spaced apart from the endocardium surface and/or measurements where the catheter touches the endocardium surface but such contact is not required for subsequent calculations based on the measurement). The same governing equations and calculations can be applied for measurements that are taken at the surface of the chamber in order to determine information at locations on the surface that were not directly probed. In other words, it is possible to collect multiple contact unipolar or potential measurements and use the same formulation to derive bipolar or current density EAM of the entire chamber. Similarly, a combination of contact and non-contact measurements can be used and the method disclosed would still apply.

The relationship between bipolar measurement and current density is described below. In addition, two methods for providing an estimation of bipolar measurement are described herein. The first method uses a unipolar potential based inverse engine to estimate bipolar signal. The second method provides a means to compute bipolar measurement or current density directly from measured electrode potentials. Each of these methods is described in more detail below following a description of the relationship between bipolar measurements and current density.

Current Density and Bipolar Signal

Figure 2:
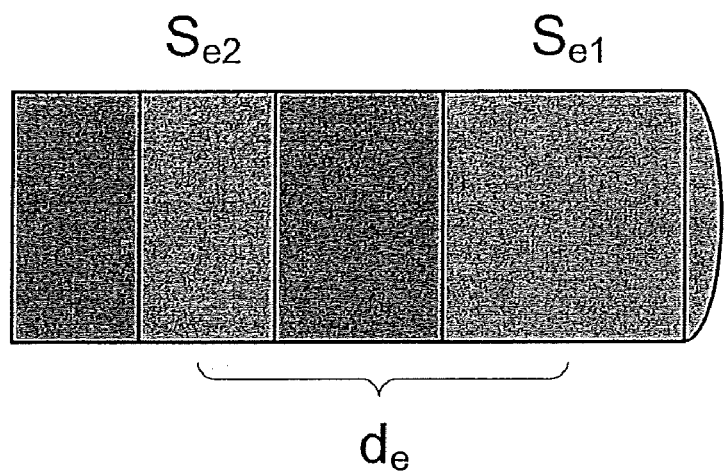
FIG. 2 is a diagram of a bipolar catheter tip.

As the distance between electrodes and their physical size diminish in a bipolar catheter, the bipolar measurement becomes proportional the electric field vector (which in turn is proportional to the current density vector) in the given catheter orientation. FIG. 2 shows an exemplary tip of a bipolar catheter that includes two electrodes. As shown in FIG. 2, $S_{e1}$ and $S_{e2}$ represent the surface area of the bipolar electrodes, and $d_e$ represents the distance between the centers of electrodes.

As $S_{e1}$, $S_{e2}$ and $d_e$ approach zero, the bipolar measurement is directly proportional to the current density. In a typical catheter, these dimensions are a few millimeters, such that a bipolar catheter can be viewed as estimating an electric field, which in a homogenous conductor such as blood is directly proportional to the current vector. It therefore follows that a current density map can be viewed as an ideal bipolar map. The map is ideal in that its value does not depend on electrode size and spacing which create inconsistencies across real physical bipolar catheters.

Indirect Solution for Bipolar Measurement

Figure 3A:
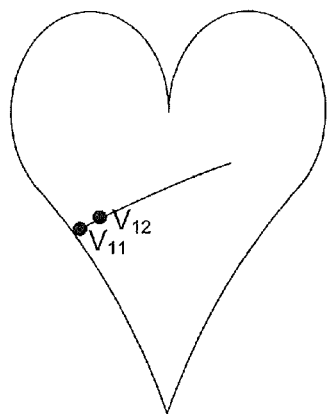
FIG. 3A is a schematic diagram of a bipolar measurement normal to the heart wall.
Figure 3B:
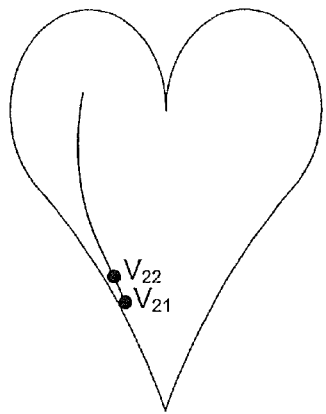
FIG. 3B is a schematic diagram of a bipolar measurement tangential to the heart wall.

One approach to obtaining bipolar measurements using a non-contact system is to subtract unipolar data from neighboring locations. Referring to FIGS. 3A and 3B, two catheter configurations which could generate bipolar measurement are shown. In the configuration of FIG. 3A, the catheter is positioned normal to the cardiac wall and in the configuration of FIG. 3B, the catheter is positioned tangential to the cardiac wall.

We note that the orientation of the bipolar electrodes relative to the heart will affect the bipolar measurement amplitude. For example, a reversed orientation (180°) will provide the negative value of the original (e.g., in FIG. 3A, the two electrodes measure signals V11 and V12, the result of subtracting V11 from V12 will be the negative of the value of subtracting V12 from V11). Furthermore, the specific tangential orientation of the catheter in FIG. 3B also affects measured amplitude. In order to avoid ambiguity relating to sign and amplitude, it is therefore preferred, but often impractical, to position the measuring catheter normal to the heart wall as in FIG. 3A when performing bipolar measurements. A key advantage of a non-contact bipolar map in this context is the ability to completely control the orientation of the bipolar estimation thereby providing a more consistent measure than in contact mapping.

In order to obtain an estimated bipolar signal from a unipolar potential inverse engine, we generate an inverse solution for surface potentials $\hat{V}_e$. As shown in FIG. 4B, for the tangential case (e.g., the case shown in FIG. 3B) two neighboring potentials with a fixed distance (e.g. 3 mm) are subtracted such that $\hat{V}_{bt} = \hat{V}_{21} - \hat{V}_{22}$.

Figure 4A:
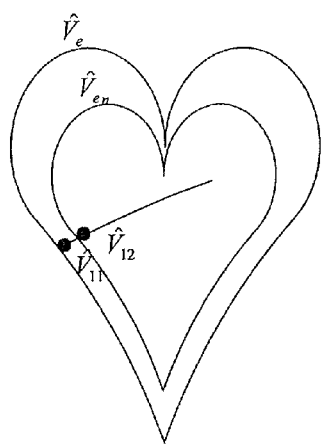
FIG. 4A-4C show schematic diagrams of a computation to estimate bipolar signal from a unipolar signal.
Figure 4B:
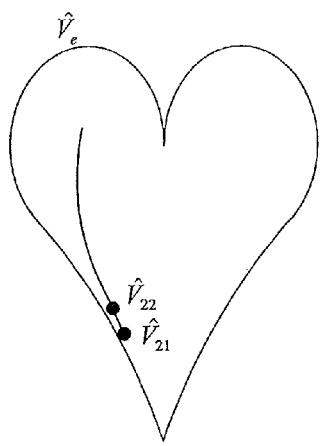
Figure 4C:
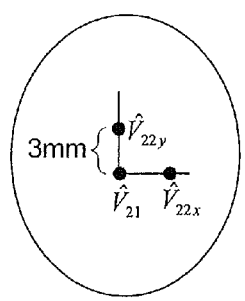

As shown in FIG. 4C, to reduce orientation dependency two orthogonal measurements tangential to the surface can be generated. In order to generate an estimated bipolar measurement invariant to tangential orientation the two magnitudes can be combined as $\hat{V}_{bt} = \sqrt{(\hat{V}_{21} - \hat{V}_{22x})^2 + (\hat{V}_{21} - \hat{V}_{22y})^2}$.

As shown in FIG. 4A, in order to generate the normal bipolar measurement (e.g., the case shown in FIG. 3A) another surface can be generated that is either an expanded or reduced version of the original surface at some distance (e.g. 3 mm) in the normal direction. The inverse problem is solved on this surface to generate $\hat{V}_{en}$. Following this step, the normal bipolar measurement is generated by subtracting corresponding elements on both surfaces such as $\hat{V}_{bn} = \hat{V}_{11} - \hat{V}_{12}$.

While the above provides a method of expanding potential inversion to provide a bipolar measurement, there is a reduction in accuracy due to regularization. When surface Tikhonov regularization is used in potential inversion, the estimation of potential distribution on the surface is smoothed by the regularization operator. The smoothing operator reduces the difference in measurement between neighboring locations, which in turn reduces and adds error to bipolar amplitude obtained in the above scheme. Therefore, in some embodiments, it can be advantageous to use a direct solver for the bipolar signal as described below.

Forward Solution Formulations

In the example provided below, the direct solution for current density is demonstrated using the finite element method. It should be appreciated that a number of other numerical methods such as boundary element, finite volume, finite difference, etc. could be used to accomplish the same goal. In the example below, after introducing some governing equations, a forward finite element formulation for the unipolar case is described, followed by a more generalized forward formulation for the potential and current density case. Additionally, and inverse operation which adds a volumetric regularization is also described below.

Governing Equations for Endocardial and Epicardial Problems

Figure 5:
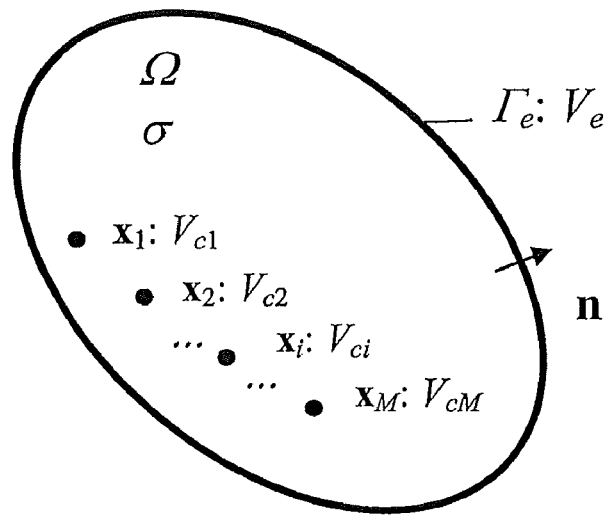
FIG. 5 is a schematic diagram of a computational domain.
Figure 6:
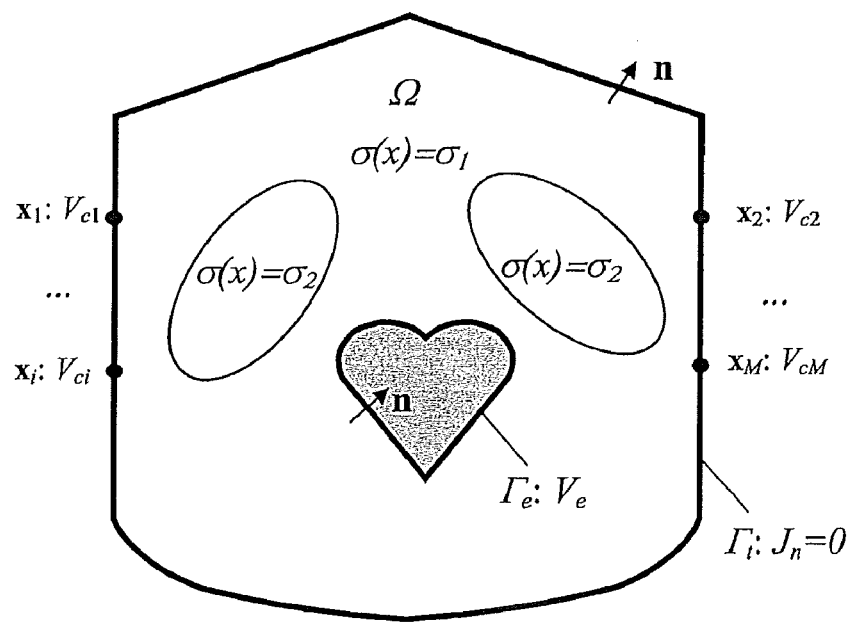
FIG. 6 is a schematic diagram of a computational domain.

FIGS. 5 and 6 show schematic representations of the endocardial and epicardial problems of electrocardiography, respectively. To model such problems, the underlying electromagnetic equations are the stationary electroquasistatic Maxwell's equations. The technical literature also refers to such problems as stationary conduction or simply conduction problems. This approximation is justified for the endocardial and epicardial problems of electrocardiography because at frequencies of such problems the electric and magnetic fields are decoupled and the displacement currents can be neglected.

A stationary conduction forward problem is formulated by three Maxwell's equations:

$$\nabla \times E = 0 \quad (0.1)$$

$$\nabla \cdot J = 0 \quad (0.2)$$

$$J = \sigma(x) E \quad (0.3)$$

Equation (0.1) expresses that the electric field E is conservative. Thus, E can be described by a scalar electric potential $\Phi$ as follows:

$$E = -\nabla \Phi \quad (0.4)$$

Equation (0.2) states that the current density vector J is source free in the intracavitary domain and (0.3) is the differential Ohm's law. In the following description, it is assumed that the electric conductivity $\sigma(x)$ is spatially varying, thereby treating both the endocardial and epicardial problems simultaneously. The endocardial solution to this problem is useful for intracardiac mapping which can be used in minimally invasive procedures such as catheter ablation. The epicardial problem is useful for non-invasive body surface based EAM which can be used to diagnose myocardial infarction and other heart disease. For the sake of simplicity, as used herein, $\sigma$ denotes general spatial variation.

FIG. 5 shows a model of a typical endocardial problem. Substituting (0.3), (0.4) into (0.2), results in a representation of the Laplace equation, the governing equation for the scalar unipolar potential as follows:

$$-\nabla \cdot (\sigma \nabla \Phi) = 0 \text{ in } \Omega \quad (0.5)$$

By prescribing the electric scalar unipolar potential on the endocardium, $$\Phi = V_e \text{ on } \Gamma_e \text{ (endocardium)} \quad (0.6)$$

a boundary value problem (BVP) is obtained, the so-called Dirichlet problem, which has a well-posed unique solution.

The other problem is the epicardial problem of electrocardiography, which is depicted in FIG. 6. The formulation of this problem is described below. The governing equation can be represented by the equation (0.5) as in the case of endocardial problems but with spatially varying electric conductivity. This spatial variation models the different tissue regions in the torso. The boundary conditions are:

$$\Phi = V_e \text{ on } \Gamma_e \text{ (epicardium)} \quad (0.7)$$

$$-\sigma \frac{\partial \Phi}{\partial n} = 0 \text{ on } \Gamma_t \quad (0.8)$$

where $\Gamma_e$ and $V_e$ now denote the epicardial surface and the epicardial unipolar potential, respectively. Equation (0.8) expresses the fact that no current flows through the torso surface $\Gamma_t$ and it is called the homogeneous Neumann boundary condition. It is well established that the BVP (0.5), (0.7) and (0.8) also has a unique and stable solution.

As shown below in the following two subsections, the boundary condition (0.8) does not explicitly appear in the finite element formulation (so comes the alternative name natural boundary condition). Therefore, the solution of endocardial problems with spatially varying electric conductivity, can be applied without modification to epicardial body surface problems as well.

On the endocardium or epicardium—depending on the type of the problem—different types of EAM's can be generated. One way is to display the electric potential, $V_e$. As explained above, it can be advantageous to also compute current density based EAM's which are proportional to the bipolar measurement. Three options of expressing the current density are described below. One is to display the magnitude of the current density vector $$J = |J| = \sqrt{J_x^2 + J_y^2 + J_z^2} \quad (0.9)$$

A second option is to consider only the normal component of the current density $$J_n = J \cdot n \quad (0.10)$$

where n is the unit normal vector of the endocardial or epicardial surfaces. A third option is to represent the magnitude of the tangential component of the current density $$J_t = |J - J \cdot n| \quad (0.11)$$

The total and tangential magnitudes, J and $J_t$, loose "sign" information while $J_n$ retains it.

Electric Scalar Potential (Unipolar) Formulation

Weak Form of the Forward Problems

In order to derive the solution algorithm of the Dirichlet problem by the finite element method, the solution below begins by introducing the weak forms of the endocardial and epicardial BVP's (0.5), (0.6) and (0.5), (0.7), (0.8), respectively. Beginning with the endocardial problem, multiply equation (0.5) by an arbitrary admissible weighting function w with vanishing value on the endocardium and integrate the product over the whole domain $\Omega$ $$-\int_\Omega w \nabla \cdot (\sigma \nabla \Phi) d\Omega = 0 \quad (0.12)$$

By applying the vector identity $$-w\nabla \cdot a = \nabla w \cdot a - \nabla \cdot (wa) \quad (0.13)$$

with $a=-\sigma\nabla\Phi$ and the Gauss's law, the following equation is obtained $$\int_\Omega \nabla w \cdot \sigma \nabla \Phi d\Omega - \underbrace{\int_{\Gamma_e} w\sigma \frac{\partial \Phi}{\partial n} d\Gamma}_{=0} = 0 \quad w = 0 \text{ on } \Gamma_e \quad (0.14)$$

where the second term is zero due to the vanishing weighting functions on the endocardial surface.

The weak form for the Laplace epicardial problem (0.5), (0.7), (0.8) can be derived similarly $$\int_\Omega \nabla w \cdot \sigma \nabla \Phi d\Omega - \underbrace{\int_{\Gamma_e} w\sigma \frac{\partial \Phi}{\partial n} d\Gamma}_{=0} - \underbrace{\int_{\Gamma_t} w\sigma \frac{\partial \Phi}{\partial n} d\Gamma}_{=0} = 0 \quad (0.15)$$

$$w = 0 \text{ on } \Gamma_e$$

where the first surface term is zero due to the vanishing weighting functions on the epicardial surface similarly to the endocardial case in (0.14). The natural boundary condition (0.8) can be "weakly" enforced by setting the second surface term in (0.15) to zero. We can conclude that the weak forms of the endocardial and epicardial problems (0.14), (0.15) are in the same form if spatially varying electric conductivity were assumed. Thus, the examples below discuss the finite element discretization and the inverse solutions of the endocardial problem only and the results can be applied to the epicardial problem straightforwardly by simply substituting endocardial surface with epicardial surface.

In order to handle non-zero Dirichlet boundary conditions, the electric vector potential can be split into two parts $$\Phi = \Phi_e + \Phi_a, \Phi_e = V_e, \Phi_a = 0 \text{ on } \Gamma_e \quad (0.16)$$

where the only requirement for the volumetric function $\Phi_e$ is to have the same value as the prescribed surface potential $V_e$ on the endocardium but arbitrary otherwise. By substituting (0.16) into (0.14) the following equation is obtained:

$$\int_\Omega \nabla w \cdot \sigma \nabla \Phi_a d\Omega = -\int_\Omega \nabla w \cdot \sigma \nabla \Phi_e d\Omega \quad (0.17)$$

for all $w$: $w = 0$ on $\Gamma_e$

Equation (0.17) is called the weak form of the Dirichlet problem (0.5), (0.6). This means that if (0.17) is satisfied for any admissible weighting function w then $\Phi = \Phi_e + \Phi_a$ is the solution of the BVP (0.5), (0.6).

Finite Element Discretization of Laplace Equation

Equation (0.17) provides a starting point for the finite element formulation. By interpolating $\Phi$:

$$\Phi = \sum_{n \in \mathbb{N}} \Phi_n \alpha_n \quad (0.18)$$

where $\alpha_n$ is a linear nodal interpolation function associated with vertex n as illustrated in FIG. 7. $\mathbb{N}$ denotes the set of vertex numbers in the volumetric tetrahedral mesh and $\Phi_n$ are the nodal potential values. In this linear case, the interpolation functions are equal to the volume—or affine—coordinates $\lambda_n$ of the tetrahedrons $$\alpha_n = \lambda_n \quad (0.19)$$

The split (0.16) can easily be realized by the finite element interpolation scheme $$\Phi = \sum_{n \in \mathbb{N}_e} \Phi_n \alpha_n + \sum_{n \in \mathbb{N}_a} \Phi_n \alpha_n \quad (0.20)$$

where $\mathbb{N}_e$ and $\mathbb{N}_a$ are the sets of endocardial and intracavitary vertex numbers, respectively. By substituting (0.20) into (0.17) and using the intracavitary finite element interpolation functions as weighting functions, the following equation is obtained:

$$\int_\Omega \nabla \alpha_m \cdot \sigma \nabla \left( \sum_{n \in \mathbb{N}_a} \Phi_n \alpha_n \right) d\Omega = -\int_\Omega \nabla \alpha_m \cdot \sigma \nabla \left( \sum_{n \in \mathbb{N}_e} \Phi_n \alpha_n \right) d\Omega \quad (0.21)$$

$$m \in \mathbb{N}_a$$

By changing the order of the integration and summation the following equation is generated:

$$\sum_{n \in \mathbb{N}_a} \Phi_n \int_\Omega \nabla \alpha_m \cdot \sigma \nabla \alpha_n d\Omega = -\sum_{n \in \mathbb{N}_e} \Phi_n \int_\Omega \nabla \alpha_m \cdot \sigma \nabla \alpha_n d\Omega \quad (0.22)$$

$$m \in \mathbb{N}_a$$

By choosing the intracavitary interpolation functions as weighting functions in (0.21) the constraint for the weighting functions in (0.14) is satisfied automatically. Equation (0.22) is a symmetric algebraic equation system and it can be written in a compact form $$[K_{aa}][\Phi_a] = -[K_{ae}][\Phi_e] \quad (0.23)$$

where $$[K_{aa}]_{mn} = \int_\Omega \nabla \alpha_m \cdot \sigma \nabla \alpha_n d\Omega; \ m, n \in \mathbb{N}_a \quad (0.24)$$

$$[K_{ae}]_{mn} = \int_\Omega \nabla \alpha_m \cdot \sigma \nabla \alpha_n d\Omega; \ m \in \mathbb{N}_a, n \in \mathbb{N}_e \quad (0.25)$$

and $[\Phi_a]$ and $[\Phi_e]$ are column vectors with the intracavitary and endocardial nodal potentials. With such nodal finite element representation, $[\Phi_e] = [V_e]$ thus (0.23) becomes $$[K_{aa}][\Phi_a] = -[K_{ae}][V_e] \quad (0.26)$$

Equations system (0.26) is a positive definite linear system for the intracavitary nodal potential values and can be solved uniquely.

Direct Solution for Current Density—Scalar Potential Mixed Formulation

Governing Equations for the Mixed Formulation

There are several alternative ways to formulate the electric conduction problem (0.1)-(0.3). Our goal is to use a formulation where the current density J is explicitly computed together with the scalar potential. In order to achieve that, we write the conduction problem (0.1)-(0.3) in a "mixed" form that includes two equations $$\frac{1}{\sigma} J + \nabla \Phi = 0 \qquad (0.27)$$

$$\nabla \cdot J = 0 \qquad (0.28)$$

Equations (0.27), (0.28) with the boundary condition (0.6) is also a well-posed BVP with a unique solution. The advantage of this formulation can be that it provides both the current density and the electric potential without the need of any further differentiation.

Weak Form of the Mixed Formulation

To obtain the finite element discretization, we have to first obtain the weak form of the system (0.27), (0.28). Let us multiply (0.27) with an arbitrary vector weighting function W and integrate over $\Omega$ $$\int_\Omega \frac{1}{\sigma} W \cdot J \, d\Omega + \int_\Omega W \cdot \nabla \Phi \, d\Omega = 0 \qquad (0.29)$$
$$\text{for all } W: \nabla \cdot W \in L^2(\Omega)$$

where $L^2(\Omega)$ is the function space of square integrable functions in $\Omega$. If we utilize the vector identity (0.13) again, we arrive at $$\int_\Omega \frac{1}{\sigma} W \cdot J \, d\Omega + \int_\Omega \nabla \cdot W \Phi \, d\Omega + \int_{\Gamma_e} W \cdot n \Phi \, d\Gamma = 0 \qquad (0.30)$$

Similarly, multiply (0.28) by a scalar weighting function w and integrate over the domain $$\int_\Omega w \nabla \cdot J \, d\Omega = 0 \text{ for all } w: w = 0 \text{ on } \Gamma_e \qquad (0.31)$$

If equations (0.30), (0.31) are satisfied for all admissible vector and scalar weighting functions W and w, J and $\Phi$ are the solutions of the BVP (0.27), (0.28). This means that the weak forms (0.30), (0.31) are equivalent to the strong problem (0.27), (0.28), respectively. Note that the same formulation can be used for the epicardial problem.

Finite Element Discretization

In order to obtain the finite element equations, we proceed similarly to the scalar potential formulation. We interpolate the scalar potential by linear nodal finite elements as in (0.20). In order to obtain a unique solution, we have to use linear facet finite element functions $$J = \sum_f J_f \beta_f \qquad (0.32)$$
where
$$\beta_f = \beta_{mno} = 2(\lambda_m \nabla \lambda_n \times \nabla \lambda_o + \lambda_n \nabla \lambda_o \times \nabla \lambda_m + \lambda_o \nabla \lambda_m \times \nabla \lambda_n) \qquad (0.33)$$

and $J_f$ are unknown facet current density coefficients. Note that the interpolation form (0.33) ensures the desired property of weighting functions in (0.29). The facet interpolation functions are illustrated in FIG. 8 Each interpolation function belongs to a triangle facet in the tetrahedral mesh. The most important property of such a vector function is that the integral of its normal component is 1 on the triangle that is associated with and 0 on the other 3 triangles of the tetrahedron. This property ensures that the continuity of the normal component of the current density (0.32) is satisfied everywhere in the volumetric mesh automatically. A representation by (0.33) is called divergence conforming representation.

Let us plug (0.32), (0.20) into (0.30), (0.31), and use the vector and nodal interpolation functions as weighting functions. After changing the order of the summations and integrations, we obtain $$\sum_{f \in \mathbb{N}_T} J_f \int_\Omega \frac{1}{\sigma} \beta_e \beta_f \, d\Omega - \sum_{n \in \mathbb{N}_a} \Phi_n \int_\Omega \nabla \cdot \beta_e \alpha_n \, d\Omega = \qquad (0.34)$$
$$\sum_{n \in \mathbb{N}_e} \Phi_n \left( \int_\Omega \nabla \cdot \beta_e \alpha_n \, d\Omega - \int_{\Gamma_e} \beta_e \cdot n \alpha_n \, d\Gamma \right); \quad e \in \mathbb{N}_T$$

$$-\sum_{f \in \mathbb{N}_T} J_f \int_\Omega \alpha_m \nabla \cdot \beta_f \, d\Omega = 0 \quad m \in \mathbb{N}_a \qquad (0.35)$$

Equations (0.34), (0.35) can be written in compact form $$\begin{bmatrix} K_{TT} & K_{Ta} \\ K_{aT} & 0 \end{bmatrix} \begin{bmatrix} J_T \\ \Phi_a \end{bmatrix} = \begin{bmatrix} K_{Te} & 0 \\ 0 & 0 \end{bmatrix} \begin{bmatrix} V_e \\ 0 \end{bmatrix} \qquad (0.36)$$
where $$[K_{TT}]_{ef} = \int_\Omega \frac{1}{\sigma} \beta_e \beta_f \, d\Omega; \; e, f \in \mathbb{N}_T \qquad (0.37)$$

$$[K_{Ta}]_{en} = -\int_\Omega \nabla \cdot \beta_e \alpha_n \, d\Omega; \; e \in \mathbb{N}_T; n \in \mathbb{N}_a \qquad (0.38)$$

$$[K_{aT}] = [K_{Ta}]^T \qquad (0.39)$$

$$[K_{Te}]_{en} = \int_\Omega \nabla \cdot \beta_e \alpha_n \, d\Omega - \int_\Omega \beta_e \cdot n \alpha_n \, d\Gamma; \; e \in \mathbb{N}_T; n \in \mathbb{N}_e \qquad (0.40)$$

Equation system (0.36) has a unique solution and it provides the current density and scalar potential simultaneously.

Inverse Algorithm for Current Density and Electric Scalar Potential Simultaneously Inversion in Terms of Electric Scalar Potential In order to illustrate how the inverse conduction problems of electrocardiography can be formulated when finite element discretization is utilized, the electric scalar potential formulation (0.22) provides a starting point. As described above, only the endocardial inverse problem shown in FIG. 5. is discussed in detail. Assume that the catheter points coincide with the vertices of a volumetric tetrahedral mesh of the computational domain. This can easily be achieved by generating a mesh in which the catheter points are vertices of the mesh. Denote the set of catheter vertex numbers by $\mathbb{N}_c$ and the rest of the volume vertex numbers by $\mathbb{N}_{\bar{c}}$. Note that $\mathbb{N}_a = \mathbb{N}_c \cup \mathbb{N}_{\bar{c}}$.

The inverse finite element equation can be formed by rearranging the equation system (0.22) to have the catheter vertices on the right hand side $$\sum_{n \in \mathbb{N}_{\bar{c}}} \Phi_n \int_\Omega \nabla \alpha_m \cdot \sigma \nabla \alpha_n \, d\Omega + \sum_{n \in \mathbb{N}_e} \Phi_n \int_\Omega \nabla \alpha_m \cdot \sigma \nabla \alpha_n \, d\Omega = \quad (2.1)$$

$$-\sum_{n \in \mathbb{N}_c} \Phi_n \int_\Omega \nabla \alpha_m \cdot \sigma \nabla \alpha_n \, d\Omega \quad m \in \mathbb{N}_a$$

As above, we can write this equation in a compact form:

$$[K_{a,\bar{c}e}][\Phi_{\bar{c}e}] = -[K_{ac}][V_c] \quad (2.2)$$

Equation (2.2) is severely ill-posed and introduction of regularization is needed to solve it.

We have stated previously that all the results for the endocardial forward problem are valid for the epicardial problem without modification. This is also true for the inverse discussion of the epicardial inverse problems. Then $\mathbb{N}_c$ denotes the set of vertex numbers on the torso surface where measurements are available and $\mathbb{N}_{\bar{c}}$ contains the rest of the torso-surface and volumetric vertex numbers as shown in FIG. 6.

Inversion by Mixed Formulation

In this subsection, a formulation of the solution of the endocardial inverse problem in terms of the mixed formulation (0.27), (0.28) is shown. One advantage of the mixed formulation is that it provides both the endocardial current density and scalar unipolar potential simultaneously. Furthermore, this formulation couples the two physical quantities as part of its regularization scheme.

Similarly to the rearrangement in the scalar potential case, (0.34), (0.35) can be rearranged as $$\sum_{f \in \mathbb{N}_T} J_f \int_\Omega \frac{1}{\sigma} \beta_e \beta_f \, d\Omega - \sum_{n \in \mathbb{N}_{\bar{c}}} \Phi_n \int_\Omega \nabla \cdot \beta_e \alpha_n \, d\Omega - \quad (2.3)$$

$$\sum_{n \in \mathbb{N}_e} \Phi_n \left( \int_\Omega \nabla \cdot \beta_e \alpha_n \, d\Omega - \int_{\Gamma_e} \beta_e \cdot n \alpha_n \, d\Gamma \right) =$$

$$\sum_{n \in \mathbb{N}_c} \Phi_n \int_\Omega \nabla \cdot \beta_e \alpha_n \, d\Omega; \quad e \in \mathbb{N}_T$$

$$-\sum_{f \in \mathbb{N}_T} J_f \int_\Omega \alpha_m \nabla \cdot \beta_f \, d\Omega = 0 \quad m \in \mathbb{N}_a \quad (2.4)$$

These equations can also be written in a compact form as:

$$\begin{bmatrix} K_{TT} & K_{T,\bar{c}e} \\ K_{aT} & 0 \end{bmatrix} \begin{bmatrix} J_T \\ \Phi_{\bar{c}e} \end{bmatrix} = \begin{bmatrix} K_{Tc} & 0 \\ 0 & 0 \end{bmatrix} \begin{bmatrix} V_c \\ 0 \end{bmatrix} \quad (2.5)$$

The difficulty is that equation (2.5) is ill-posed and needs regularization to obtain a solution.

It can be beneficial to utilize the unipolar potential formulation 2.2) as regularization thereby coupling the estimated current to scalar unipolar potential. This is substituted into the zero block of the system matrix (2.5) as a regularization matrix multiplied by a regularization parameter $$\begin{bmatrix} K_{TT} & K_{T,\bar{c}e} \\ K_{aT} & \lambda K_{a,\bar{c}e} \end{bmatrix} \begin{bmatrix} J_T \\ \Phi_{\bar{c}e} \end{bmatrix} = \begin{bmatrix} K_{Tc} & 0 \\ -\lambda K_{ac} & 0 \end{bmatrix} \begin{bmatrix} V_c \\ 0 \end{bmatrix} \quad (2.6)$$

An additional regularization for the current density J has to be added to limit the current density magnitude $$\begin{bmatrix} K_{TT} + \mu M_{TT} & K_{T,\bar{c}e} \\ K_{aT} & \lambda K_{a,\bar{c}e} \end{bmatrix} \begin{bmatrix} J_T \\ \Phi_{\bar{c}e} \end{bmatrix} = \begin{bmatrix} K_{Tc} & 0 \\ -\lambda K_{ac} & 0 \end{bmatrix} \begin{bmatrix} V_c \\ 0 \end{bmatrix} \quad (2.7)$$

where the parameter $\mu$ is another regularization parameter. The regularization matrix $[M_{TT}]$ is also a volumetric regularization matrix. One exemplary form can be represented as:

$$[M_{TT}]_{ef} = \left[ \sum_K S_K \int_{\Omega_K} \frac{1}{\sigma} \nabla \cdot \beta_e \nabla \cdot \beta_f \, d\Omega \right] \quad (2.8)$$

where $S_K = [\text{volume}(\Omega_K)]^{2/3}$ is a weighting factor and $\Omega_K$ denotes the tetrahedrons in which the integration takes place. The solution of (2.7) is well-posed and unique for J and $\Phi$ if we use reasonable values for the regularization parameters $\mu$ and $\lambda$. It is believed that, values between 0.4 and 1.0 for both regularization parameters provide increased inversion quality.

Post Processing

Various types of post-processing can be used. In some embodiments, the post processing may involve selecting a format for outputting (e.g., displaying) the reconstructed bipolar or current density information to a user. In other embodiments, the post-processing may involve significant further mathematical manipulation of the reconstructed potentials to provide additional types of physiological information.

Some of the post-processing operations performed on the reconstructed set(s) of physiological information include the generation of a resolution map. Such a resolution map indicates the spatial resolution of reconstructed physiological information at points on the endocardium surface, thereby providing a measure of the reliability and accuracy of the information at various points on the endocardium surface. Resolution maps may be used with any form of post-processing operation including all modes listed below. The resolution map may be superimposed with physiological information to highlight those areas that are accurate and those that are not. Strictly speaking, information about the resolution maps can be determined prior to obtaining the reconstructed information; however, herein we generally refer to the generation and display of the resolution map as "post-processing" because such information is typically presented to the user with reconstructed physiological information.

Another type of post-processing operation that may be performed includes the generation of isocurrent maps. Particularly, where the reconstructed physiological information pertains to bipolar or current density, the magnitude of reconstructed information may be color coded and superimposed on the 3D endocardial representation. Isocurrent maps are the reconstructed current densities computed for every sampled set of data over a single or multiple heart beats. For the magnitude either the normal, tangential or total bipolar or current density may be computed.

Another type of post-processing operation that may be performed includes the generation of vector isocurrent maps. Particularly, where the reconstructed physiological information pertains to bipolar or current density, the reconstructed information may be represented by arrows on vertices in the 3D endocardial representation. Vector isocurrent maps are the reconstructed current densities computed for every sampled set of data over a single or multiple heart beats. In this representation the length of the arrow represents magnitude while its direction is the direction of the current or bipolar vector.

Yet another type of post-processing operation includes the generation of timing maps (such as activation time maps). The timing maps provide information on the time-dependent behavior of the heart's electrical activity. Particularly, the activation map indicates at what point in time particular points on the endocardium surface experience a change in their electrical activity. For example, the activation map could identify the point in time at which particular cells on the endocardium surface experienced depolarization. Another type of timing map may be an iso-duration map where the amount of time certain tissue has been active for is detected. Timing maps may be computed from the reconstructed bipolar or current density information over a single or multiple heart beats. Timing maps may be determined and displayed for one or more points on the endocardium surface representation.

Another type of post processing operation is the generation of amplitude maps. Amplitude maps can be used to display characteristics of bipolar or current amplitude in a given area. The amplitude maps may be computed from the reconstructed bipolar or current density information over a single or multiple heart beats. Useful amplitude map information that may be determined and displayed for one or more points on the endocardium surface representation includes the maximum amplitude, or root mean square values.

Another type of post-processing operation is the generation of a difference map. The difference map provides information regarding the effectiveness of the clinical procedure (e.g., ablation) performed on the patient to ameliorate the symptoms of arrhythmias. The difference map compares the electrical behavior of the heart, as reflected from two or more voltage maps generated before and after the performance of the particular clinical procedure.

A further type of post processing operation is the generation of frequency maps. Frequency mapping, and more generally spectral analysis, are used to identify on the endocardium surface localized sites of high-frequency activity during fibrillation. Frequency maps are computed by acquiring multiple sets of reconstructed information over a particular time interval which includes a single or multiple heart beats. The acquired raw data is then used to obtain the frequency representation of that data. Specific information (e.g., dominant frequency components) from the frequency representation is subsequently identified, and that identified information may be displayed.

Other types of post-processing information may likewise be performed.

EXAMPLE

Figure 9A:
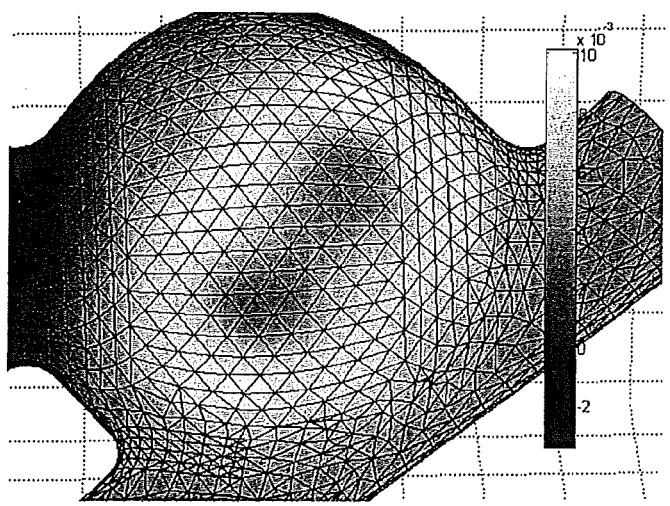
FIGS. 9A, 9B, and 9C show exemplary physiological data.
Figure 9B:
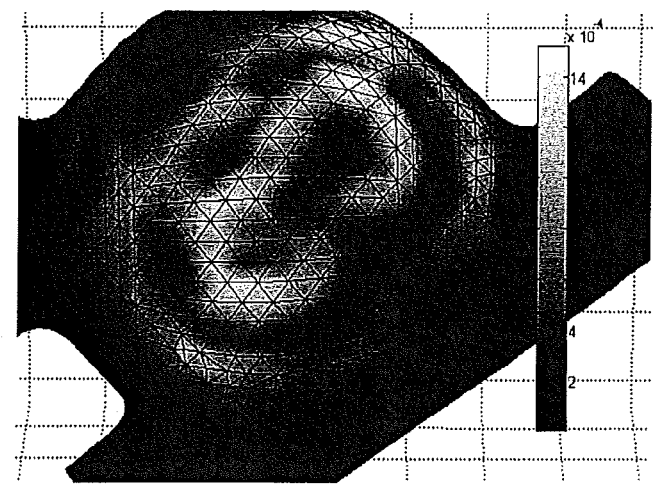
Figure 9C:
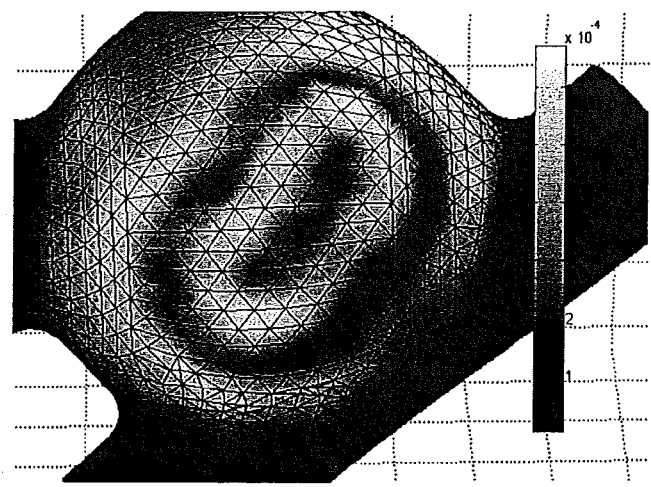

FIGS. 9A, 9B, and 9C show exemplary physiological data generated using a unipolar measurement, an indirect solution for bipolar measurement, and a direct solution for bipolar measurement, respectively.

In order to generate the exemplary physiological data shown in FIGS. 9A-9C, a catheter carrying a multi-electrode array was used for collecting unipolar signals inside a model of a cardiac chamber placed in a saline bath. A known electrical activation sequence was driven on the surface of the model, simulating a real electrical activation of a cardiac chamber. The catheter was connected to a signal acquisition system and moved around in the model, collecting signals from different locations.

The dataset that was collected was used to generate several maps for comparing different computational methodologies including generating of a unipolar measurement, an indirect solution for bipolar measurement, and a direct solution for bipolar measurement.

FIG. 9A shows a unipolar map that was generated using the methodology described in U.S. Pat. No. 7,515,954 entitled "Non-contact cardiac mapping, including moving catheter and multi-beat integration" and filed Jun. 13, 2006 which is hereby incorporated in its entirety by reference. Though high in quality, since this map displays unipolar information this map can be less intuitive to physicians who are accustomed to viewing bipolar information. In addition, this unipolar map (based on unipolar measurements) is affected by far field.

FIG. 9B shows a bipolar map generated using the indirect approach described above. This is an example of the tangential approach generated from the unipolar map (e.g., generation of bipolar information based on a unipolar potential map). While this map is believed to be advantageous to the unipolar map, its quality is inferior to the quality of the direct solution (FIG. 9C) due to smoothing that takes place in the intermediate step of solving the unipolar problem.

FIG. 9C shows a bipolar map generated using the direct approach described above. This is an example of the tangential approach generated directly from the unipolar measurements made by the catheter. The direct approach presents similar type of information as the indirect approach (FIG. 9B). This information is bipolar information which is believed to be more useful than the unipolar information. Furthermore, it can be observed that the direct method produces an improved map showing finer details.

Representative System

Figure 10:
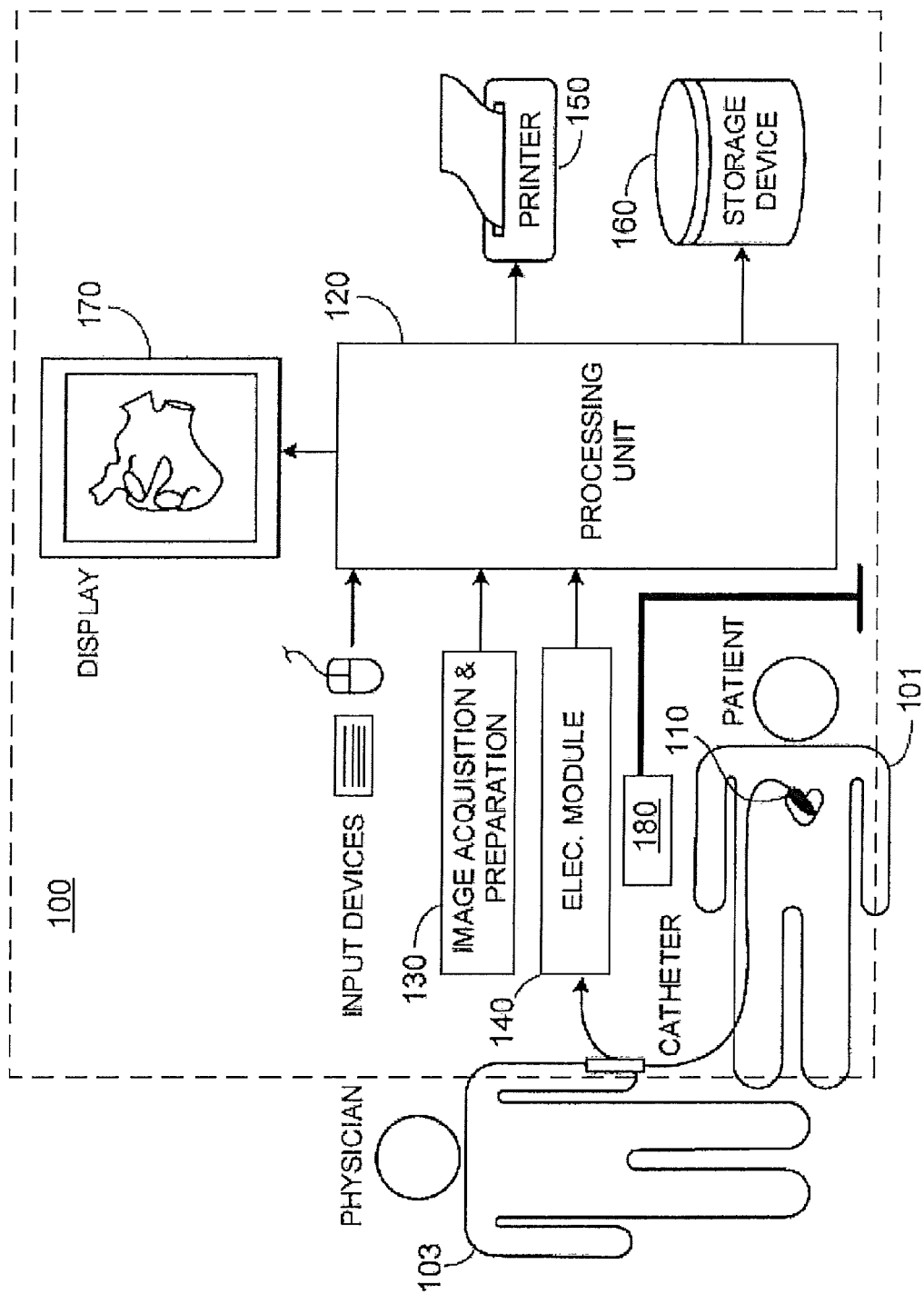
FIG. 10 is a schematic diagram of an exemplary system.

FIG. 10 shows a schematic diagram of an exemplary embodiment of a mapping system 100. The system 100 includes a moveable catheter 110 having multiple spatially distributed electrodes. During the signal acquisition stage of the mapping procedure the catheter 110 is displaced to multiple locations within the heart chamber into which catheter 110 is inserted.

In some embodiments the distal end of the catheter 110 is fitted with multiple electrodes spread somewhat uniformly over the catheter. For example, the electrodes may be mounted on the catheter 110 following a 3D olive shape. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, or shape memory material such as Nitinol.

At each of the locations to which the catheter 110 is moved, the catheter's multiple electrodes acquire signals resulting from the electrical activity in the heart cavity. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements are synchronized with one another so that the measurement are performed at approximately the same phase of the heart cycle. The signal measurements over multiple beats can be synchronized based on features detected from physiological data such as surface ECG or intracardiac electrograms.

Mapping system 100 further includes the processing unit 120 which performs several of the operations pertaining to the mapping procedure, including the reconstruction procedure to determine the physiological information at the surface (e.g., as described above). To expedite the computational operations performed by the mapping system 100, the processing unit 120 can compute, generally prior to the insertion of the catheter into the heart chamber and/or before signal acquisition by the catheter's electrodes has commenced, transformation functions that can be used in real-time to facilitate the reconstruction process. Once the catheter 110 is inserted and is displaced to a particular location in the heart chamber, the mapping procedure can be performed expeditiously by computing in real-time those transformation components that were not computed ahead of the signal acquisition stage, and combining those components with the appropriate pre-processed transformation components to obtain the overall transformation function(s). That overall transformation function is applied to the acquired raw data to perform the inverse reconstruction operation.

The processing unit 120 also performs a catheter registration procedure. The location of the catheter 110 inserted into the heart chamber can be determined using a conventional sensing and tracking system (not shown) that provide the 3D spatial coordinates of the catheter and/or its multiple electrodes with respect to the catheter's coordinate system as established by the sensing and tracking system. However, to perform the mapping procedure and reconstruct physiological information on the endocardium surface, it is necessary to align the coordinate system of the catheter 110 with the endocardium surface's coordinate system. The processing unit 120 (or some other processing module of system 100) determines a coordinate system transformation function that transforms the 3D spatial coordinates of the catheter's locations into coordinates expressed in terms of the endocardium surface's coordinate system, or vice-versa.

The processing unit 120 also performs post-processing operations on the reconstructed physiological information to extract and display useful features of the information to the operator of the system 100 and/or other persons (e.g., a physician).

As further shown in FIG. 10, the signals acquired by the multiple electrodes of catheter 110 are passed to the processing unit 120 via the signal conditioning module 140. The signal conditioning module 140 receives the signals communicated from the catheter 110 and performs signal enhancement operations on the signals before they are forwarded to the processing unit 120. Signal conditioning hardware is used to amplify, filter and continuously sample intracardiac potential measured by each electrode. The intracardiac signals typically have a maximum amplitude of 60 mV, with a mean of a few millivolts. In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal can be filtered to remove the frequency corresponding to the power supply (e.g., 60 Hz). Other types of signal processing operations such as spectral equalization, automatic gain control, etc. may also take place. The resultant processed signals are forwarded by the module 140 to the processing unit 120 for further processing.

As further shown in FIG. 10, the mapping system 100 also includes peripheral devices such as printer 150 and/or display device 170, both of which are interconnected to the processing unit 120. Additionally, the mapping system 100 includes storage device 160 that is used to store data acquired by the various interconnected modules, including the volumetric images, raw data measured by electrodes and the resultant endocardium representation computed there from, the partially computed transformations used to expedite the mapping procedures, the reconstructed physiological information corresponding to the endocardium surface, etc.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Accordingly, other embodiments are within the scope of the following claims.

What is claimed is:

1. A method comprising:
inserting a catheter into a heart cavity, the catheter comprising a first electrode;
positioning a second electrode in a stable location relative to the heart, the location being outside of the heart cavity and located at a distance from the heart cavity;
for multiple different catheter positions in the heart cavity, measuring the unipolar signals by measuring a potential between the first electrode located in the heart cavity and the second electrode located outside the heart cavity;
generating bipolar information based on three or more of the unipolar signal measurements; and
displaying an electro-anatomical map of at least a portion of the heart, the electro-anatomical map including at least some of the bipolar information.

2. The method of claim 1, wherein the unipolar measurements comprise unipolar potential signals.

3. The method of claim 1, the bipolar information comprises current information.

4. The method of claim 1, wherein the bipolar information comprises current density information.

5. The method of claim 4, wherein the current density information comprises a normal component of the current density.

6. The method of claim 4, wherein the current density information comprises a magnitude of a current density vector.

7. The method of claim 4, wherein the current density information comprises a magnitude of a tangential component of the current density.

8. The method of claim 2, wherein the second electrode is located at a distance from the heart cavity such that the electrode is not affected by local tissue activation in a heart cavity.

9. The method of claim 2, wherein measuring the unipolar signals comprises measuring the unipolar signals in response to electrical activity in a heart cavity.

10. The method of claim 2, wherein generating a bipolar measurement based on three or more unipolar measurements comprises determining bipolar information at multiple locations of a surface based on the unipolar signals and positions of one or more electrodes used to measure the unipolar signals with respect to the surface.

11. The method of claim 2, wherein generating the bipolar information comprises applying a transformation function to the unipolar signals.

12. The method of claim 11, wherein applying the transformation function comprises solving directly for current.

13. The method of claim 1, wherein generating the bipolar information comprises solving simultaneously for current and potential.

14. A system comprising:
a processing unit configured to:
receive unipolar measurements, the unipolar measurements comprising potentials measured between a first electrode located in a heart cavity and a second electrode located outside the heart cavity; and
generate bipolar information based on three or more of the unipolar measurements; and
a display unit configured to:
display an electro-anatomical map of at least a portion of a heart, the electro-anatomical map including at least some of the bipolar information.

15. A method comprising:
inserting a catheter into a heart cavity, the catheter comprising one or more electrodes;
positioning an electrode in a stable location relative to the heart, the location being outside of the heart cavity and located at a distance from the heart cavity;
for multiple different catheter positions in the heart cavity, measuring potentials between the one or more electrodes located in the heart cavity and the electrode located outside the heart cavity;
generating current density information at multiple locations of a surface based on the measured potentials and positions of the one or more electrodes located in the heart cavity with respect to the surface; and
displaying an electro-anatomical map of at least a portion of the heart, the electro-anatomical map including at least some of the current density information.

16. A method comprising:
inserting a catheter into a heart cavity, the catheter comprising a first electrode;
positioning electrodes configured to compute a Wilson's central terminal measurement in a stable location relative to the heart;
for multiple different catheter positions in the heart cavity, measuring the unipolar signals by measuring a potential between the first electrode located in the heart cavity and the Wilson's central terminal;
generating bipolar information based on three or more of the unipolar signal measurements; and
displaying an electro-anatomical map of at least a portion of the heart, the electro-anatomical map including at least some of the bipolar information.

17. The method of claim 16, wherein the unipolar measurements comprise unipolar potential signals.

18. The method of claim 16, the bipolar information comprises bipolar information selected from the group consisting of current information, current density information, a normal component of the current density, a magnitude of a current density vector, and a magnitude of a tangential component of the current density.

19. The method of claim 18, wherein measuring the unipolar signals comprises measuring the unipolar signals in response to electrical activity in a heart cavity:

20. The method of claim 16, wherein generating a bipolar measurement based on three or more unipolar measurements comprises determining bipolar information at multiple locations of a surface based on the unipolar signals and positions of one or more electrodes used to measure the unipolar signals with respect to the surface.

21. The method of claim 15, wherein the current density information comprises current density information selected from the group consisting of a normal component of the current density, a magnitude of a current density vector, and a tangential component of the current density.

22. The method of claim 15, wherein the electrode in the stable location is located at a distance from the heart cavity such that the electrode is not affected by local tissue activation in a heart cavity.

23. The method of claim 15, wherein measuring the potentials comprises measuring the unipolar signals in response to electrical activity in a heart cavity.

24. The method of claim 15, wherein generating the current density information comprises applying a transformation function to the measured potentials.

25. The method of 15, wherein the electrode in the stable location comprises one or more body-surface electrodes.

26. The method of claim 15, wherein the electrode in the stable location comprises one or more electrodes positioned in a stable location inside a body.

27. The method of 1, wherein the electrode in the stable location comprises one or more body-surface electrodes.

28. The method of 1, wherein the electrode in the stable location comprises one or more electrodes positioned in a stable location inside a body.

29. The system of claim 14, wherein the unipolar measurements comprise unipolar potential signals and the bipolar information comprises current information.

30. The system of claim 14, the bipolar information comprises bipolar information selected from the group consisting of current information, current density information, a normal component of the current density, a magnitude of a current density vector, and a magnitude of a tangential component of the current density.

31. The system of claim 14, wherein the configurations to generate the bipolar measurement based on three or more unipolar measurements comprise configurations to determine bipolar information at multiple locations of a surface based on the unipolar signals and positions of one or more electrodes used to measure the unipolar signals with respect to the surface.

32. The system of claim 14, wherein the second electrode comprises one or more body-surface electrodes.

* * * * *

UNITED STATES PATENT AND TRADEMARK OFFICE
CERTIFICATE OF CORRECTION

PATENT NO. : 8,401,625 B2  Page 1 of 1
APPLICATION NO. : 13/185699
DATED : March 19, 2013
INVENTOR(S) : Doron Harlev and Zsolt Badics It is certified that error appears in the above-identified patent and that said Letters Patent is hereby corrected as shown below:

In the Claims

Column 25, Line 61, In Claim 19, delete "cavity:" and insert -- cavity. --

Column 25, Line 17, In Claim 25, after "of" insert -- claim --

Column 25, Line 19, In Claim 26, after "of" insert -- claim --

Column 25, Line 22, In Claim 27, after "of" insert -- claim --

Column 26, Line 1, In Claim 28, after "of" insert -- claim --

Signed and Sealed this
Twenty-eighth Day of May, 2013

Teresa Stanek Rea
*Acting Director of the United States Patent and Trademark Office*